United States Patent [19] [11] 4,144,879

Nakayama et al. [45] Mar. 20, 1979

[54] BLOOD PRESSURE MEASURING INSTRUMENT

[75] Inventors: Kiyoshi Nakayama, Koganei; Shinichi Yagi, Hino, both of Japan

[73] Assignee: Zaidanhojin Nipponrodobunkakyokai, Tokyo, Japan

[21] Appl. No.: 788,097

[22] Filed: Apr. 15, 1977

[30] Foreign Application Priority Data

Apr. 19, 1976 [JP] Japan .................................. 51-44622

[51] Int. Cl.² .............................................. A61B 5/02
[52] U.S. Cl. ......................... 128/2.05 A; 128/2.05 M; 128/2.05 Q
[58] Field of Search .................... 128/2.05 A, 2.05 D, 128/2.05 F, 2.05 M, 2.05 Q, 2.05 R

[56] References Cited

U.S. PATENT DOCUMENTS

| 3,552,383 | 1/1971 | Kreuger ........................... 128/2.05 A |
| 3,654,915 | 4/1972 | Sanctuary ....................... 128/2.05 M |
| 3,903,872 | 9/1975 | Link ................................. 128/2.05 A |
| 3,985,123 | 10/1976 | Herzlinger et al. ............. 128/2.05 F |

OTHER PUBLICATIONS

Angelakos, E. T., "Semiconductor Pressure Microtransducers for Measuring Velocity and Acceleration of Intra-ventricular Pressures", Amer. Jrnl. Med. Electronics, Oct.-Dec. 1964, pp. 266-270.

George, M. et al. "Measurement of the Maximum Rate of Rise of Aortic BP in Man", Med. Research Engr., Fourth Quarter 1967, pp. 21-24.

Primary Examiner—Robert W. Michell
Assistant Examiner—Francis J. Jaworski
Attorney, Agent, or Firm—Pollock, VandeSande and Priddy

[57] ABSTRACT

A pressure is applied by pressure means to a blood vessel from the outside, and gradually reduced, and the pressure resulting from movement of the blood pressure during the pressure reduction is converted by a pressure sensor into an electric signal. The converted output is differentiated twice, and it is detected that a first-polarity pulse, a second-polarity pulse and another first-polarity pulse are generated successively in the differentiated output waveform within a predetermined period of time. The highest blood pressure is obtained with the pressure of the pressure means at the moment of first detection of three such pulses, and the lowest blood pressure is obtained with the pressure of the pressure means when the above detection is no longer achieved. The measured values are recorded in a digital form and, at the same time, the converted output waveform is recorded.

9 Claims, 14 Drawing Figures

BLOOD PRESSURE MEASURING INSTRUMENT

BACKGROUND OF THE INVENTION

This invention relates to an instrument for measuring the highest and lowest blood pressures.

In conventional sphygmomanometry, an air pressure is applied to a blood-pressure cuff wound around the upper arm until the flow of the blood stops and then the pressure of the blood-pressure cuff is gradually lowered, the moment when the blood starts to flow instantly is detected as a sound through a stethoscope and the pressure of the blood-pressure cuff at this moment is designated as the highest blood pressure. The pressure of the blood-pressure cuff is then further reduced and the pressure at the moment when the sound is no longer detected, that is, when the flow of the blood becomes steady, is designated as the lowest blood pressure. Since the flow of the blood is detected by an ear, the measurement is carried out by instinct, and is subject to each operator's individual difference and an error of about ±10 mmHg is usually found. Even if measurement is effected by a skillful person, an error of ±5 mmHg usually results, and measurement by an unskillful person is entirely untrustworthy.

To avoid such operator's individual difference, there has also been proposed an automatic blood pressure measuring instrument. This instrument is adapted to pick up the sound of the flow of the blood instead of an operator. That is, the sound is picked up by a microphone connected to the stethoscope, and recorded and, at the same time, the pressure of the blood-pressure cuff is recorded. From these records, the pressure at the moment when the sound was detected by the stethoscope for the first time and the pressure at the moment when the sound was no longer detected, are read out. However, this conventional instrument is very low in accuracy. That is, in the case of hearing the sound through the stethoscope, noises can be discerned according to their tones, but when the sound is converted by the microphone into an electric signal, the correct sound cannot be distinguished from such noises and external noises are picked up and recorded as they are. Accordingly, the record is not reliable and the correct sound is buried in the external noises. As a result of this, the accuracy of measurement is merely about ±10 mmHg, which is lower than that obtainable with the skillful person in the case of directly hearing through the stethoscope. Further, this conventional instrument of the type converting the sound into the corresponding electric signal has the disadvantage that the conditions for measurement such as the thickness of the arm and environments exert influence upon the records. In the prior art instrument, the blood flows a little each time the blood pressure reaches the highest pressure, and contraction of the blood vessel by the pulse-like flow of the blood is received as an acoustic signal, which is converted into an electric signal. Namely, the pressure fluctuation in the blood vessel is not detected as a direct signal but a secondary change is detected, and this also leads to the lowered accuracy of measurement.

An object of this invention is to provide a blood pressure measuring instrument which is capable of achieving highly accurate blood pressure measurement with a simple construction.

Another object of this invention is to provide a blood pressure measuring instrument which records the results of measurement both in an analog form and in a digital form.

Another object of this invention is to provide a blood pressure measuring instrument which automatically effects measurement only by a starting operation, with a blood-pressure cuff wound around the upper arm of an examinee.

Still another object of this invention is to provide a blood pressure measuring instrument which automatically achieves periodic measurement, with a blood-pressure cuff wound around the upper arm of an examinee.

SUMMARY OF THE INVENTION

In accordance with this invention, a blood-pressure cuff is wound around, for instance, the upper arm, a pressure sensor for converting a pressure into an electric signal is disposed inside of the blood-pressure cuff, an air pressure is applied to the blood-pressure cuff to stop the flow of the blood, and then the pressure of the blood-pressure cuff is gradually reduced. The converted output from the pressure is differentiated twice by differentiation circuits and a waveform composed of three successive pulses, namely a first-polarity pulse, a second-polarity pulse and another first-polarity pulse, is detected from the differentiated output. This detected waveform will hereinafter be called the K pulse. The pressure of the blood-pressure cuff (hereinafter referred to as the cuff pressure) at the moment when the K pulse is detected for the first time is measured. This is the highest blood pressure. And the pressure at the moment when the K pulse is no longer obtained is measured, and this is the lowest blood pressure. These measured values are displayed in a digital form, and also recorded on a recording paper. On the recording paper, the abovesaid converted output is also recorded by an analog recorder at the same time. As is evident from pulsation, the blood flows in a pulse-like manner, and the pressure which is applied to the converting element by the pressure of the blood tending to flow, is increased to produce a pulse at the output of the converting element. But when the pressure of the blood-pressure cuff is gradually reduced, the blood flows only at the peak of its highest pressure and the instant the blood flows, the pressure to the converting element lowers instantly, so that a negative gap appears in the rising-up portion of the output pulse of the pressure sensor. The time when a gently falling waveform begins to appear after the gap sharply rises is the moment at which the blood starts flowing. The waveform having such a gap is composed of three successive pulses, i.e. the first-polarity, the second-polarity and another first-polarity pulse, obtained by differentiating the aforesaid converted output twice. Consequently, the cuff pressures at the moments of obtaining the first and the last K pulse are the highest and the lowest blood pressure. Further, by observing the analog recorded waveform of the converted output, the blood pressure can be measured based on the moment of the gap generation.

By constituting a control circuit with hardware or with a simple program processor such as a micro computer so that application of a pressure to the blood-pressure cuff up to a certain value, gradual reduction of the pressure, detection of the K pulse from the converted output, and measurement and recording of the pressure cuff following the detection of the K pulse, may be automatically performed one after another by a start signal, the blood pressure can be automatically measured only by effecting the starting operation. By generating starting instructions with a constant period, the blood pressure of, for example, a post-operative patient can be automatically measured and recorded.

BRIEF DESCRIPTION OF THE DRAWINGS

FIGS. 7A to 7H and 8A and B are waveform diagrams explanatory of the operation of an auxiliary circuit portion in FIG. 4;

DESCRIPTION OF THE PREFERRED EMBODIMENT

Figure 1:
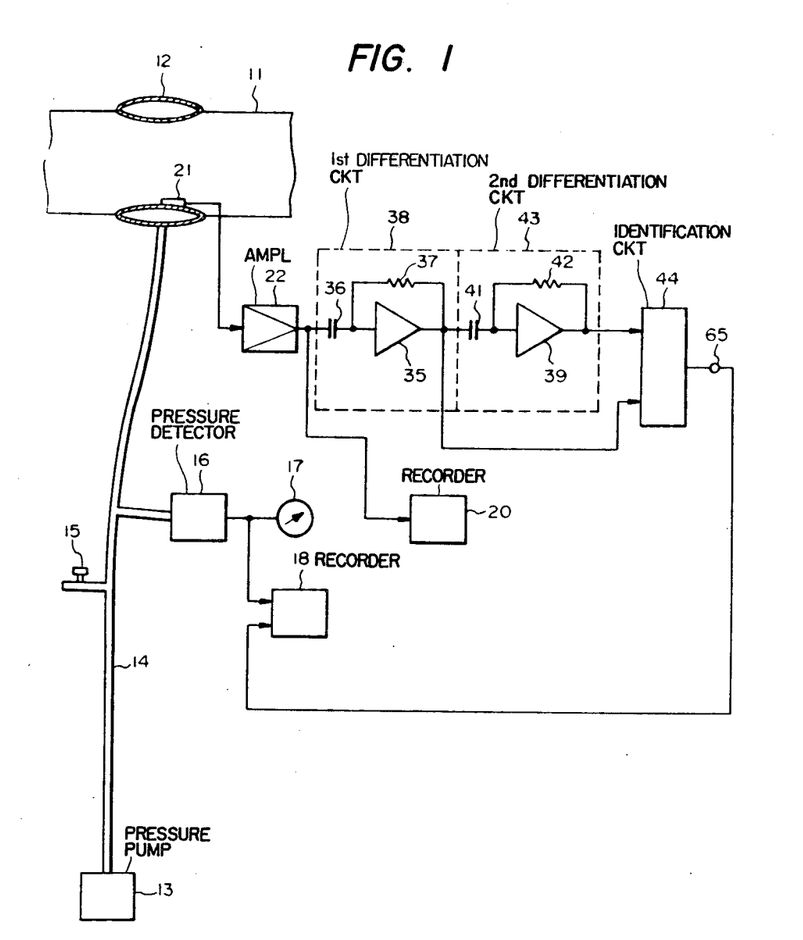
FIG. 1 is a block diagram illustrating an embodiment of a blood pressure measuring instrument according to this invention.

With reference to the drawings, a blood pressure measuring instrument according to this invention will hereinafter be described. In FIG. 1, reference numeral 11 indicates the upper arm of a man, around which a blood-pressure cuff 12 is wound. From a pressure pump 13, an air pressure is applied through a pipe 14 to the blood-pressure cuff 12 to raise its pressure and hence press hard the upper arm, thereby stopping the flow of the blood in an internal vein. The pipe 14 has a leak valve 15, by which the air pressure is always reduced to some extent, so that when the operation of the pump 13 is stopped, the pressure of the blood-pressure cuff 12 gradually lowers. The pipe 14 is also connected to a pressure detector 16, by which the pressure of the blood-pressure cuff 12 is converted into an electric signal, and indicated by an indicator 17 and recorded by a recorder 18.

On the inner side of the blood-pressure cuff 12, a pressure sensor 21 is provided for generating an electric signal in response to a change in the pressure of the blood vessel. The pressure sensor 21 is preferred to be one wherein the stiffness of its converting part is sufficiently large to convert even low frequency components close to DC components into an electric signal. For instance, a semiconductor strain gauge can be employed and this may be as small as about 20 mm in diameter and about 3 mm thick. The pressure sensor 21 is disposed at a position where pulsebeats can be obtained, and in particular, at such a location where the flow of the blood in the vein is stopped when the pressure is raised and the pulsebeats can be obtained downstream of the position of the stopped blood flow. The output from the pressure sensor 21 is amplified by an amplifier 22 as occasion demands. The output from the amplifier 22 is supplied to a pen analog recorder 20.

Figure 2:
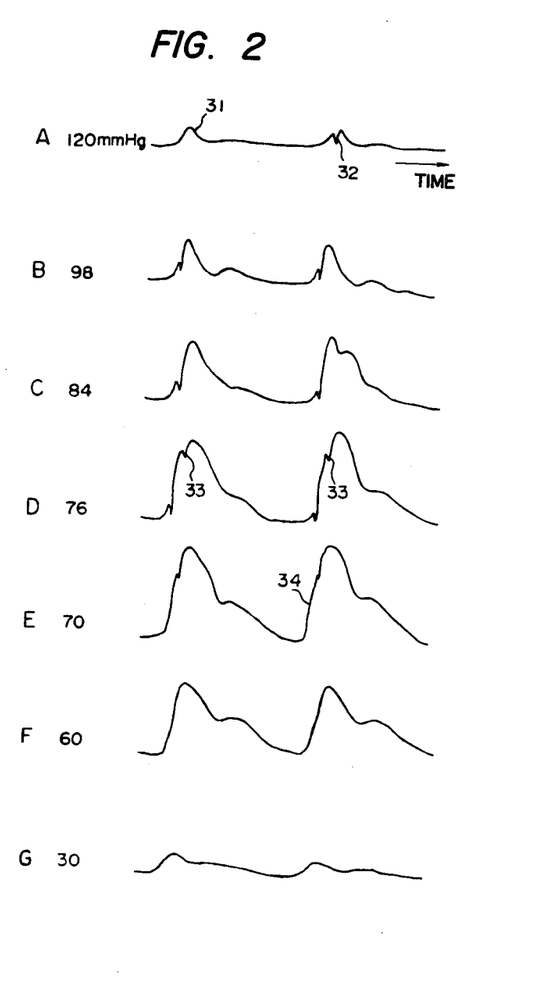
FIGS. 2A to 2G show the output waveforms of a pressure-sensor used in FIG. 1.

Recorded waveforms by the recorder 20 are shown in FIG. 2. In FIG. 2A, the left-hand pulse 31 is one that a pressure applied by a pulsation of the stopped blood to the blood-pressure cuff 12 is detected by the pressure sensor 21. In the right-hand pulse, a negative gap 32 appears in its rise-up portion. The reason for this is as follows: The blood flows in a pulse-like manner, that is, the blood flows only at the peak of the pressure with which the blood tends to flow and the blood pulse reaches one end of the pressure sensor 21 to dent it to equivalently produce a negative pressure, and then the pressure sensor 21 at large is pressed against the blood-pressure cuff 12 by the blood pulse. The passage of the blood pulse is fairly rapid and the rise of its output is appreciably sharp. Such a waveform which has a negative gap appearing at the beginning of its rise and sharply rises, indicates that the blood pulse has passed the position where the blood-pressure cuff 12 is disposed. From FIG. 2 it will be seen that as the pressure of the blood-pressure cuff 12 is lowered, its output pulse width increases, that is, the period of passage of the blood becomes gradually longer. In FIG. 2D, two negative gaps appear in each pulse waveform and it is considered that a second gap 33 is produced by the blood pulse which has returned from the periphery of a capillary vessel after once having passed the position of the pressure sensor 21. Accordingly, when the gap at the beginning of the rise of the waveform disappears, it is indicated that the blood begins to incessantly flow from the state of the right-hand pulse 34 in FIG. 2E, and this is the lowest blood pressure. In this way, the highest and the lowest blood pressures are measured by observing the waveforms recorded by the recorder 20.

The state of an intermittent flow of the blood in the record is obtained by processing the waveform of the output from the amplifier 22. To this end, the output from the amplifier 22 is differentiated twice. That is, in the illustrated example, the output from the amplifier 22 is differentiated by a first differentiation circuit 38 composed of an operational amplifier 35, a capacitor 36 and a resistor 37, and then the output from the first differentiation circuit 38 is differentiated by a second differentiation circuit 43 composed of an operational amplifier 39, a capacitor 41 and a resistor 42. The output from the differentiation circuit 43 is applied to an identification circuit 44, which detects an output wherein three pulses successively appear in the order of a negative pulse, a positive pulse and a negative pulse.

That is, when the cuff pressure is high, blood does not flow at first and, at each pulsation, such a pulse as indicated by 31 in FIG. 2 which has no gap is derived from the pressure sensor 21. But when the blood tends to flow and actually begins to flow, the negative gap 32 appears. A pulse 45 having the gap 32 is shown in FIG. 3A on an enlarged scale. The output from the first differentiation circuit 38 which has differentiated the above waveform is depicted in FIG. 3B. In the second differentiated waveform obtained from the second differentiation circuit 43 having differentiated the output from the first differentiation circuit 38, a negative pulse 46, a positive pulse 47 and a negative pulse 48 appear in this order, as shown in FIG. 3C. Accordingly, the identification circuit 44 detects that such three pulses, i.e., negative, positive and negative, as shown in FIG. 3C are generated one after another in a predetermined period of time.

Figure 3:
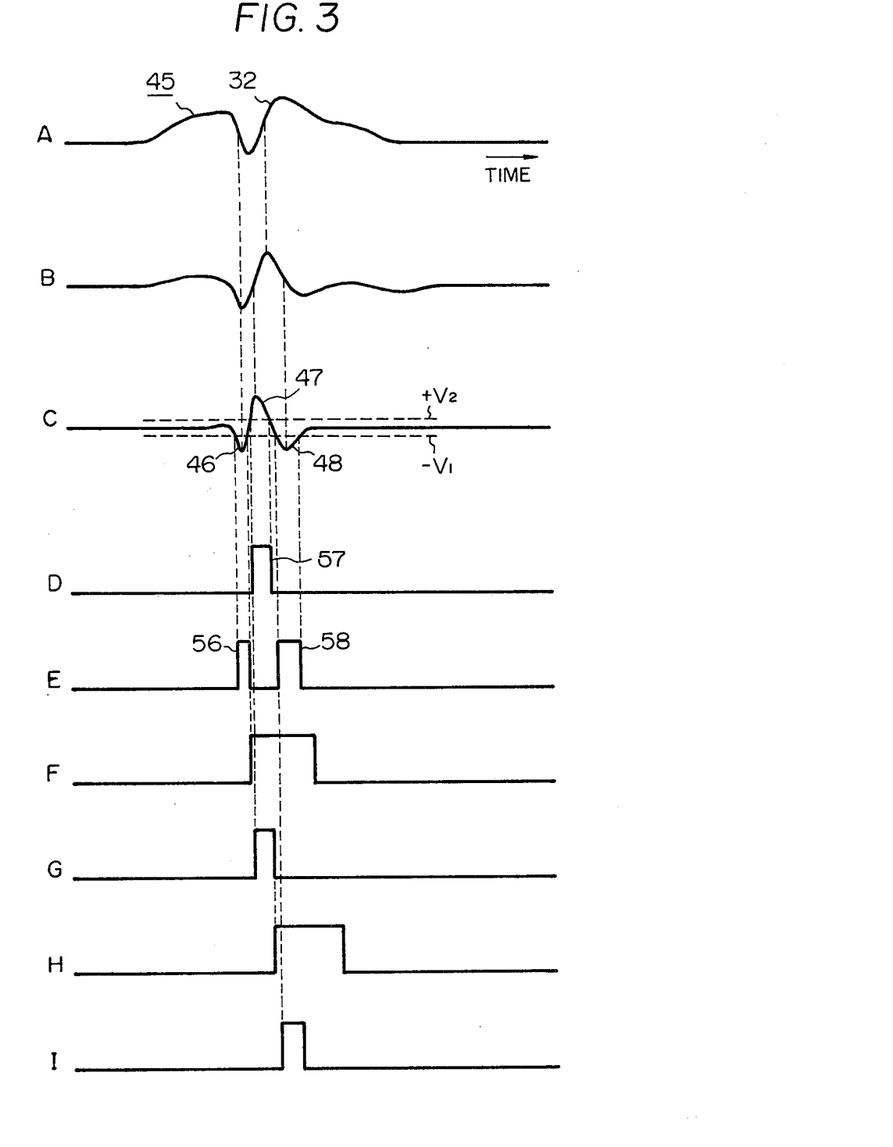
FIGS. 3A to 3I are waveform diagrams explanatory of the operation of a differentiation circuit and an identification circuit employed in FIG. 1.
Figure 4:
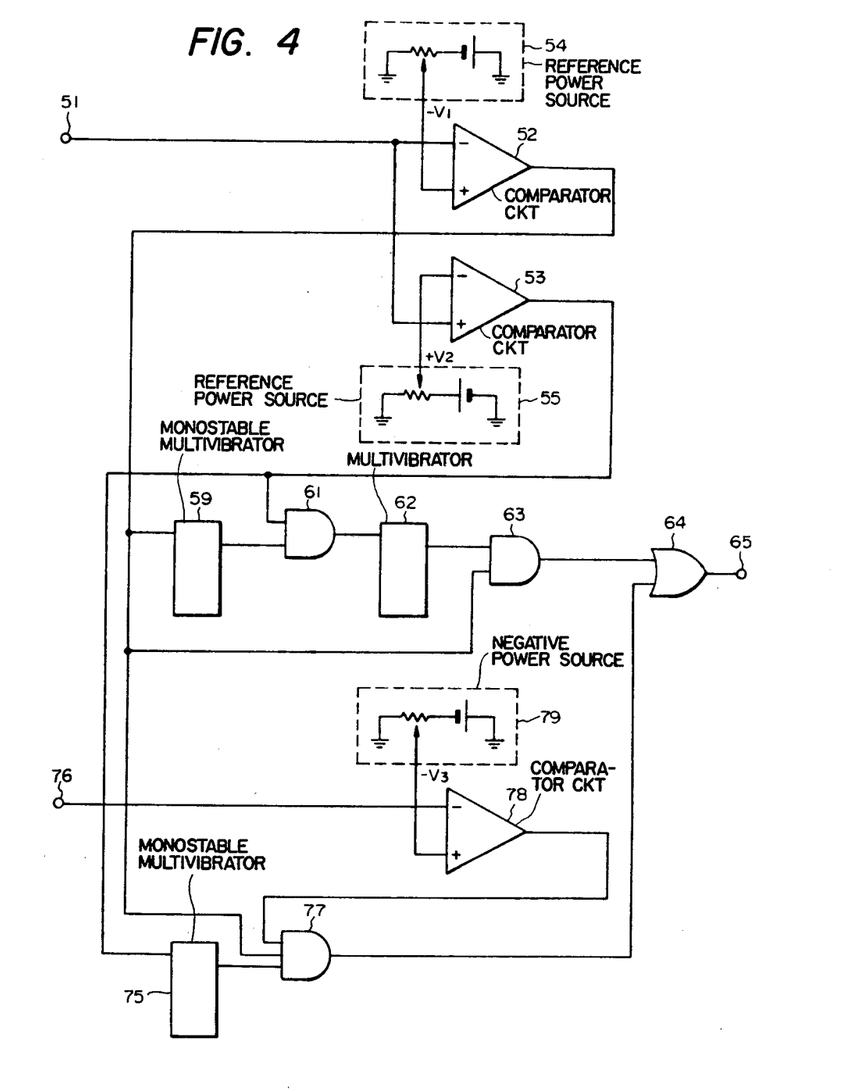
FIG. 4 is a block diagram showing an example of the identification circuit used in FIG. 1.

In the identification circuit 44, as depicted in FIG. 4, the second differentiated output signal from the differentiation circuit 43 depicted in FIG. 1 is applied from a terminal 51 to an inverted input terminal of a comparator circuit 52 and a non-inverted input terminal of a comparator circuit 53, respectively. To the non-inverted input terminal of the comparator 52, a negative constant voltage $-V_1$ is applied from a reference power source 54. And the inverted input terminal of the comparator circuit 53 is supplied with a positive constant voltage $+V_2$ from a reference power source 55. Consequently, the comparator circuit 52 detects those negative portions of the second differentiated waveform which are lower in level than the negative voltage $-V_1$, that is, the negative pulses 46 and 48 depicted in FIG. 3C, producing pulses 56 and 58 corresponding to the negative pulses 46 and 48 as shown in FIG. 3E. On the other hand, the comparator circuit 53 detects from the second differentiated waveform a positive portion whose level is higher than the positive voltage $V_2$, that is, the positive pulse 48, which is detected as a pulse 57, as illustrated in FIG. 3D.

The trailing edge of the pulse 56 derived from the comparator circuit 52 corresponding to the first negative pulse 46, drives a monostable multivibrator 59 to provide a pulse shown in FIG. 3F which has a pulse width of, for instance, 50 milliseconds, by which a gate 61 is opened. That is, the positive pulse closely following the pulse 56 is detected. The gate 61 is supplied with the output from the comparator circuit 53, and when the output is derived from the comparator circuit 53 while the multivibrator 59 produces a pulse output, the pulse 57 is detected, as illustrated in FIG. 3G. The trailing edge of this pulse drives a multivibrator 62 to provide a gate pulse having a pulse width of 50 milliseconds as shown in FIG. 3H, during which the second negative pulse 48 is detected. In other words, a gate 63 is opened by the output from the multivibrator 62 and supplied with the output from the comparator circuit 52. Thus, the negative pulse corresponding to the pulse 48 is detected by the gate 63 as depicted in FIG. 3I, and applied to an OR gate 64 to derive the aforementioned K pulse at an output terminal 65. With the output at the output terminal 65, the pressure of the pressure detector 16 is recorded as the numerical value by the recorder 18. The cuff pressure recorded for the first time after the start of reduction of the cuff pressure is the highest blood pressure. And when such second differentiated waveform including the triad of negative, positive and negative pulses disappear, that is, when the K pulse disappears, the pressure of the blood-pressure cuff 12 is indicative of the lowest blood pressure at which the flow of the blood has become a steady flow. This is the lowest blood pressure. Accordingly, the lowest blood pressure can be known from the recorded value of the recorder 18 which indicates the pressure of the blood-pressure cuff 12 when the output is no longer obtained from the terminal 65.

Figure 5:
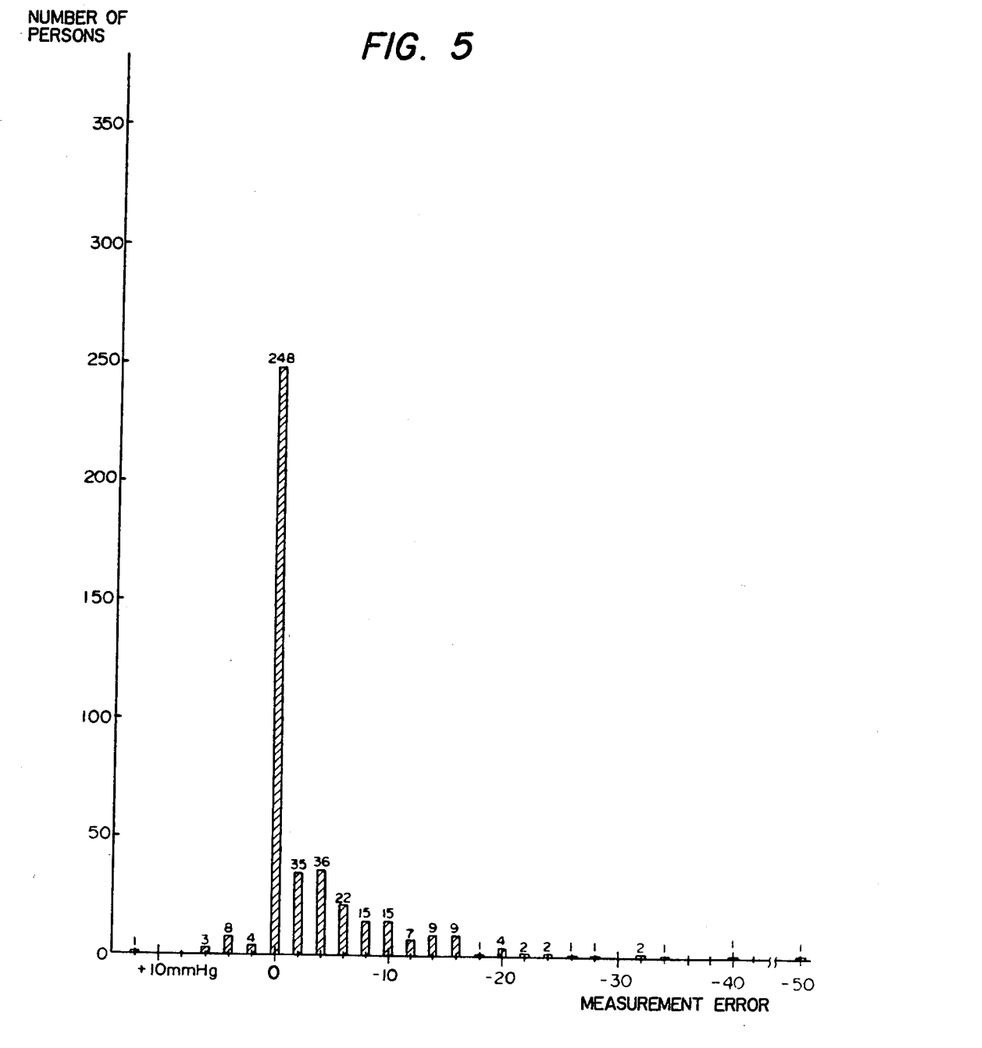
FIG. 5 is a graph showing highest blood pressure measurement error distribution.
Figure 6:
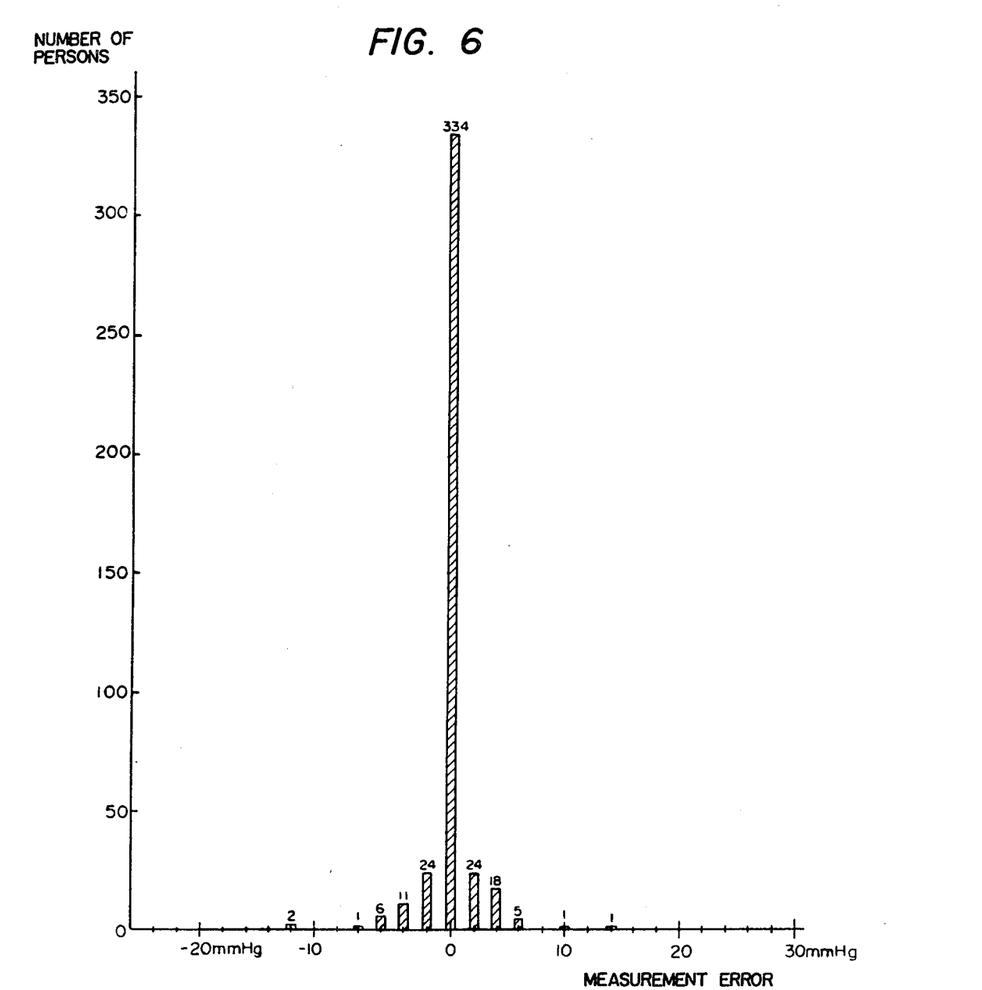
FIG. 6 is a graph showing the lowest blood pressure error distribution.

In this manner, the highest and lowest blood pressure can be accurately measured without relying upon human perception. The results of measurement of the blood pressures of 427 persons are as shown in FIG. 5 for the highest blood pressure and in FIG. 6 for the lowest blood pressure. Viewing the minimum blood pressure, 99% of the measured values are within ±6 mmHg. Where an allowable measurement error is ±6 mmHg, acceptable measured values accounts for 99%. The accuracy of measurement of the highest blood pressure is also appreciably high, but a little lower than that of the lowest blood pressure.

Figure 7:
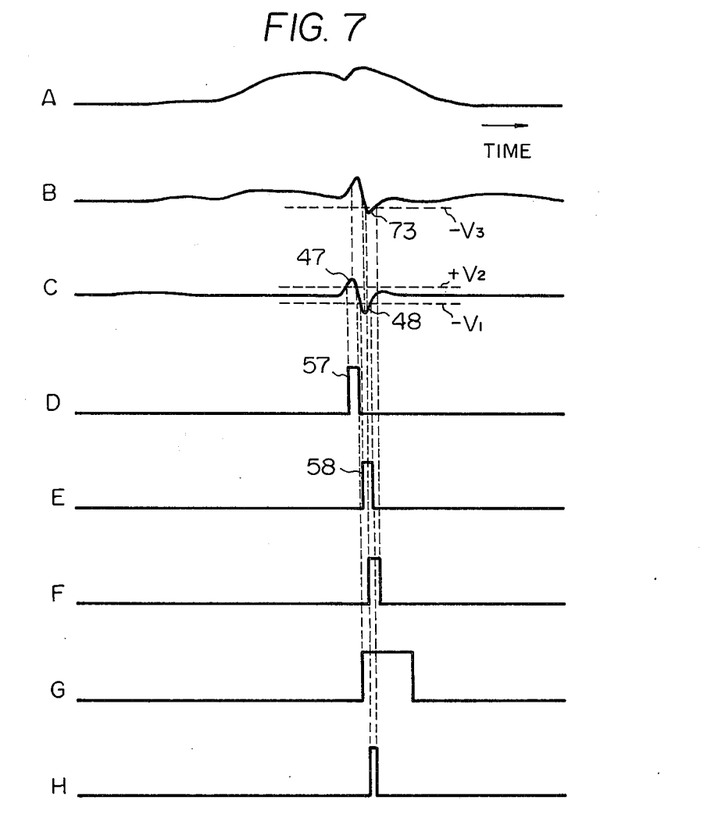
Figure 8:
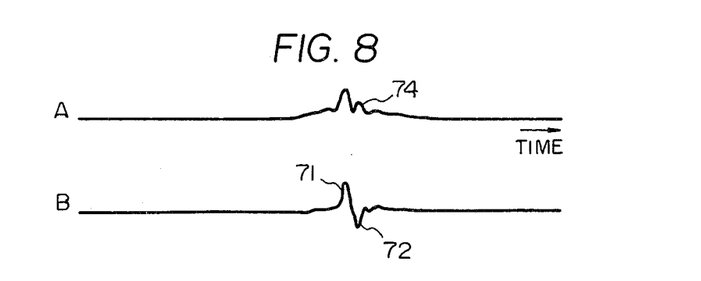

The reason is that in some of the examinees, the second differentiated waveform derived from the pressure sensor 21 did not immediately become the ideal one composed of the three pulses; negative, positive and negative, when the blood started to flow. Accordingly, more accurate measurement can be achieved in the following manner; FIG. 7A shows an example of the output waveform of the pressure sensor 21 when the blood starts to flow, FIG. 7B the first differentiated waveform of the differentiation circuit 38, and FIG. 7C the second differentiated waveform derived from the differentiation circuit 43. There are some occasions when the second differentiated waveform does not correctly become the combination of the three pulses; negative, positive and negative, that is, the first negative pulse (corresponding to pulse 46 of FIG. 3C) does not appear, as is evident from FIG. 7C. In this case, it is insufficient only to detect the combination of the positive pulse 47 and the negative pulse 48. That is, as shown in FIG. 8, the first differentiated waveform derived from the pressure sensor 21 and the second differentiated waveform when the pressure of the blood-pressure cuff 12 is lowered to achieve a flow of blood in the steady state, are such as depicted in FIGS. 8A and 8B, respectively. The second differentiated waveform is composed of a positive pulse 71 and a negative pulse 72. Accordingly, the pulse, which is produced when the flow of the blood becomes steady, is also detected. However, the first differentiated waveform shows that a negative pulse 73 is produced at the portion corresponding to the pulse 48 of the second differentiated waveform, as shown in FIG. 7B, but becomes a positive pulse 74 when the flow of the blood becomes steady, as shown in FIG. 8A. Consequently, more accurate measurement can be achieved by distinguishing them from each other.

This purpose can be attained by adding, for instance, a further circuit to the previously described circuit of FIG. 4. That is, a monostable multivibrator 75 is driven by the trailing edge of the output from the comparator circuit 53 for detecting the positive pulse 57 (FIG. 7D) to obtain a pulse output having a pulse width of 50 milliseconds, as shown in FIG. 7G, which is applied to an AND circuit 77. The AND circuit 77 is also supplied with the pulse 58 (FIG. 7E) detected by the comparator circuit 52 corresponding to the negative pulse 48 shown in FIG. 7C. Further, the first differentiated output from the first differentiation circuit 38 is applied to a comparator circuit 78 from a terminal 76, and compared with a negative reference voltage $-V_3$ from a negative power source 79. When the first differentiated output is lower than the negative reference voltage, that is, when the negative pulse 73 shown in FIG. 7B is detected, a negative pulse (FIG. 7F) is derived from the comparator circuit 78, and supplied to the AND circuit 77. Consequently, the AND circuit 77 provides a pulse shown in FIG. 7H, which is applied as the K pulse to the terminal 65 through the OR gate 64. Thus, even where the second differentiated waveform in the measurement of the highest blood pressure does not become the combination of, negative, positive and negative pulses, the highest blood pressure pulse can be correctly identified. If a permissible measurement error is ±6 mmHg, acceptable measure values share 99%.

Figure 9:
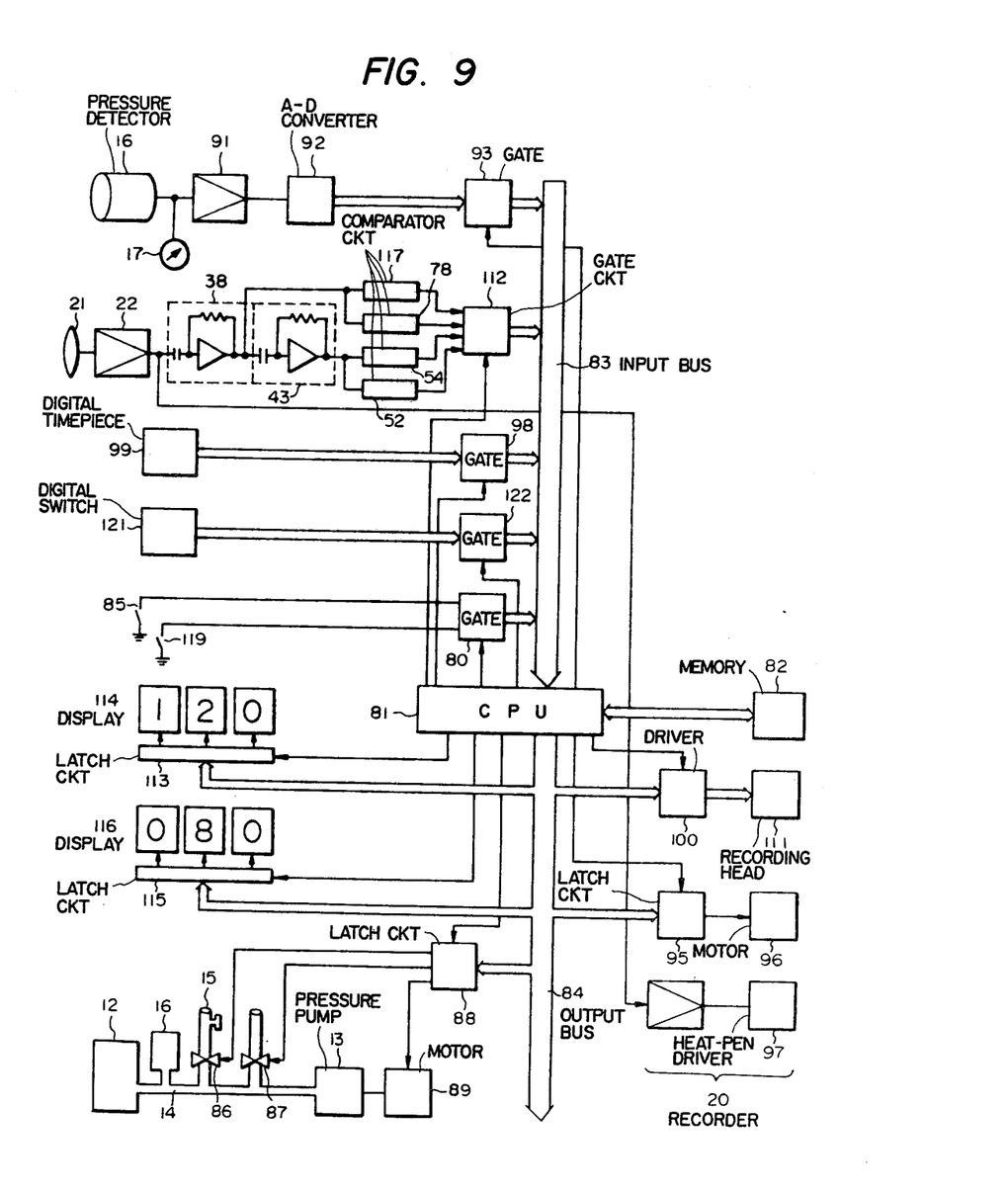
FIG. 9 is a block diagram illustrating another embodiment of the blood pressure measuring instrument according to this invention.
Figure 10:
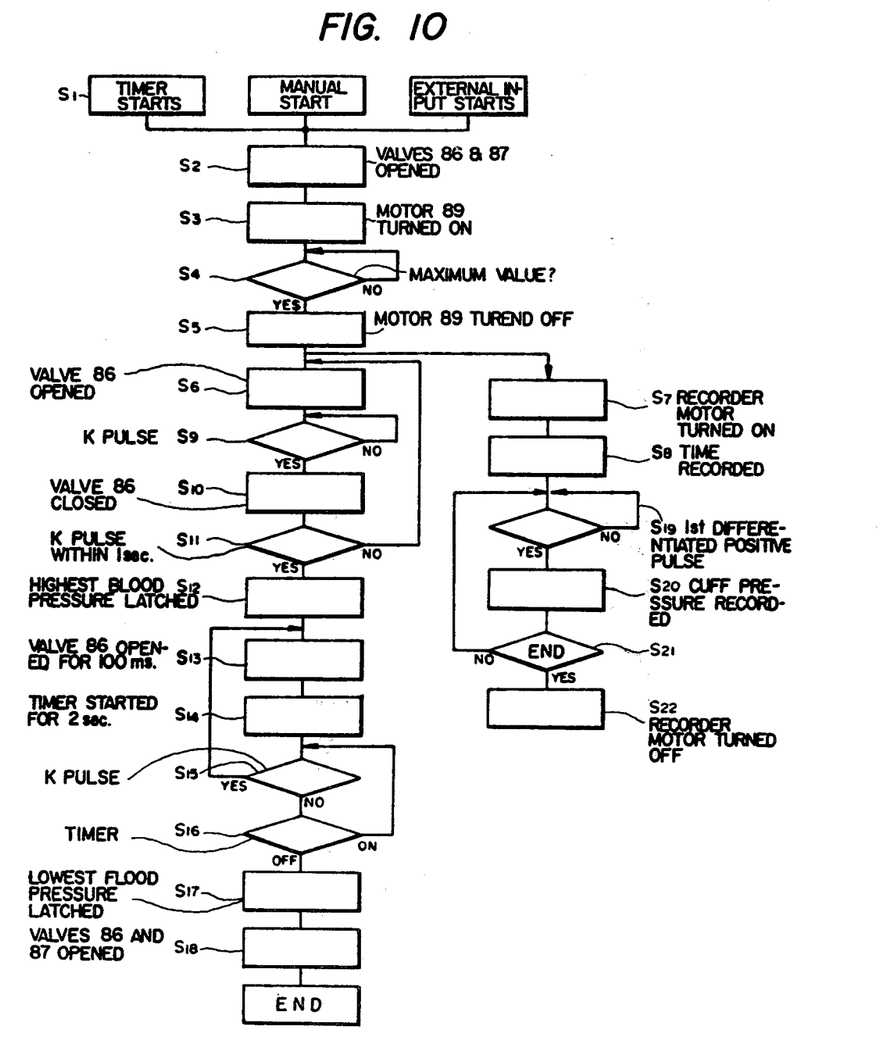
FIG. 10 is a flowchart showing an example of the procedure of its operation.

The abovesaid blood pressure measurement can also be performed automatically. FIG. 9 illustrates the case where various controls and the detection of the K pulse are effected by the employment of a micro computer which is a kind of electric computer. In FIG. 9, parts corresponding to those in FIGS. 1 and 4 are marked with the same reference numerals. A micro computer 81 has connected thereto a memory 82, which has stored therein a program necessary for various controls and detections. Further, the micro computer 81 (hereinafter referred to as the CPU 81) has connected thereto an input bus 83 supplied with input data and an output bus 84 for supplying output data. A flowchart of the control procedure is shown in FIG. 10. With reference to the flowchart, the operation of the circuit of FIG. 9 will hereinbelow be described. At a step $S_1$ in FIG. 10, where a manual start switch 85 in FIG. 9 is controlled, it is taken in the CPU 81 through the input bus 83 when a gate 80 is opened by the CPU 81. Having detected the start, the CPU 81 applies instructions through the output bus 84 to a latch circuit 88 for closing a valve 86 of the leak valve 15 and an exhaust valve 87 of the pipe 14 at a step $S_2$ in FIG. 10, thus closing the valves 86 and 87. Prior to the abovesaid starting operation, the blood-pressure cuff 12 is wound around the upper arm, with the pressure sensor 21 disposed on the inner side of the blood-pressure cuff 12. Then, at a step $S_3$ in FIG. 10, instructions for pressurizing are sent out from the CPU 81 to the output bus 84, and held in the latch circuit 88, turning a motor 89 for driving the pressure pump 13. Then, the pressure of the blood-pressure cuff 12 increases, and is converted by the pressure detector 16 into an electric signal, which is applied through an amplifier 91 to an A-D converter 92 for conversion into a digital signal. The digital signal indicative of the cuff pressure is taken in the CPU 81 through the input bus 83 by periodically controlling a gate 93 by the CPU 81, and at a step $S_4$ in FIG. 10, the digital signal is checked to determine whether or not it has reached a predetermined value. Where the highest blood pressure of an examinee is known, the abovesaid predetermined value is set to be larger than the highest blood pressure by about 20% but, in general, the predetermined value is set at about 150 to 200 mmHg and stored in the memory 82.

When the cuff pressure has reached the predetermined value, the operation proceeds to a step $S_5$, in which the motor 89 is turned off by an instruction of the CPU 81 and the valve 86 is also unlatched by an instruction of the CPU 81 to open the valve 86. Accordingly, the air in the blood-pressure cuff 12 gradually escapes from the leak valve 15 to reduce the cuff pressure. That is, the cuff pressure begins to increase at a moment $t_1$ of turning on the start switch 85, and when having reached a predetermined value Pl at a moment $t_2$, it is gradually lowered, as indicated by the curve 94 in FIG. 11. Further, simultaneously with the opening of the valve 86, instructions from the CPU 81 are applied to a latch circuit 95 through the output bus 84 to start a motor 96 for driving a recording paper of the recorder 20 at a step $S_7$. As a result of this, the output from the pressure sensor 21 is applied through the amplifier 22 to a heat pen drive part 97 of the recorder 20, thereby to start recording. Moreover, in a step $S_8$, a gate 98 is opened by instructions of the CPU 81 to supply the CPU 81 with a digital signal indicative of the time from a digital clock device 99, recording the time.

Figure 12:
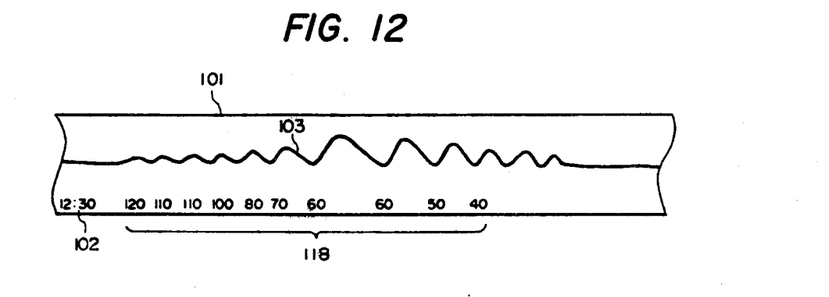
FIG. 12 is a diagram illustrating an example of a recording paper.
Figure 13:
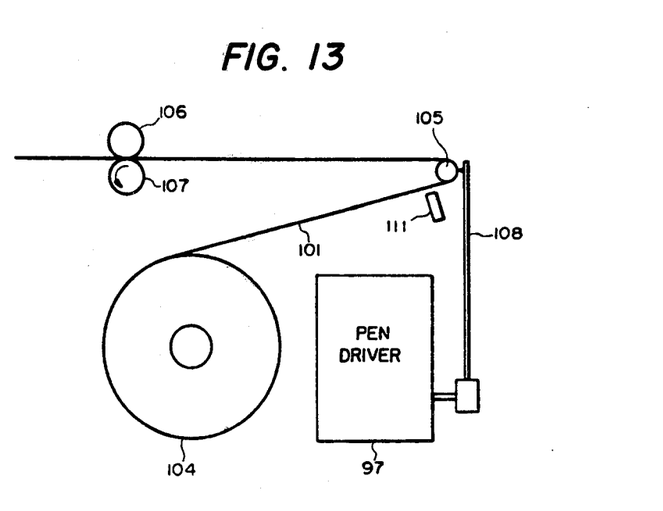
FIG. 13 is a schematic diagram showing an example of a recorder for use in this invention.

In the present example, as illustrated in FIG. 12, the time is recorded as a time indication 102 on one marginal portion of a recording paper 101 of the recorder 20 in the following manner: That is, as shown in FIG. 13, in the recorder 20, the recording paper 101, gripped between feed rollers 106 and 107, is drawn out from a supply roller 104 past a recording part 105, where recording (as indicated by 103 in FIG. 12) is achieved on the recording paper 101 by a heat pen 108 which is rotated by a pen driver 97 in the widthwise direction of the recording paper 101 in accordance with a recording signal. In the vicinity of the recording part 105, a dot-type recording head 111 is provided in contact with one marginal portion of the recording paper 101. The recording head 111 comprises seven dot-shaped recording elements arranged side by side in the widthwise direction of the recording paper 101. The recording elements divide each numeral into a matrix of seven rows and five columns, and the respective picture elements are displayed in white and black. And each numeral is recorded by the recording head 111 every column. Character codes of the 5×7 matrix for each numeral are previously stored in the memory 82, and for each numeral of the time to be recorded, the columns of the character codes are read out one after another and set in a printing latch circuit 95 through the output bus 84. In accordance with the set content, the corresponding ones of the recording elements of the recording head 111 are heated to color the recording paper 101 in the form of dots. The recording paper 101 is fed at a rate, of for example, 25 mm per second, and the recording width of one line by the recording head 111 is 20 millisecond. Such dot-type recording is well-known in the art.

Next, at a step $S_9$ in FIG. 10, the outputs from the comparator circuits 52 and 54 for respectively deriving the negative pulse and the positive pulse from the second differentiation circuit 52, and the comparator circuit 78 for deriving the negative pulse from the first differentiation circuit 38 are applied to the CPU 81 by controlling a gate 112 with instructions from the CPU 81, detecting the aforementioned K pulse.

Figure 14:
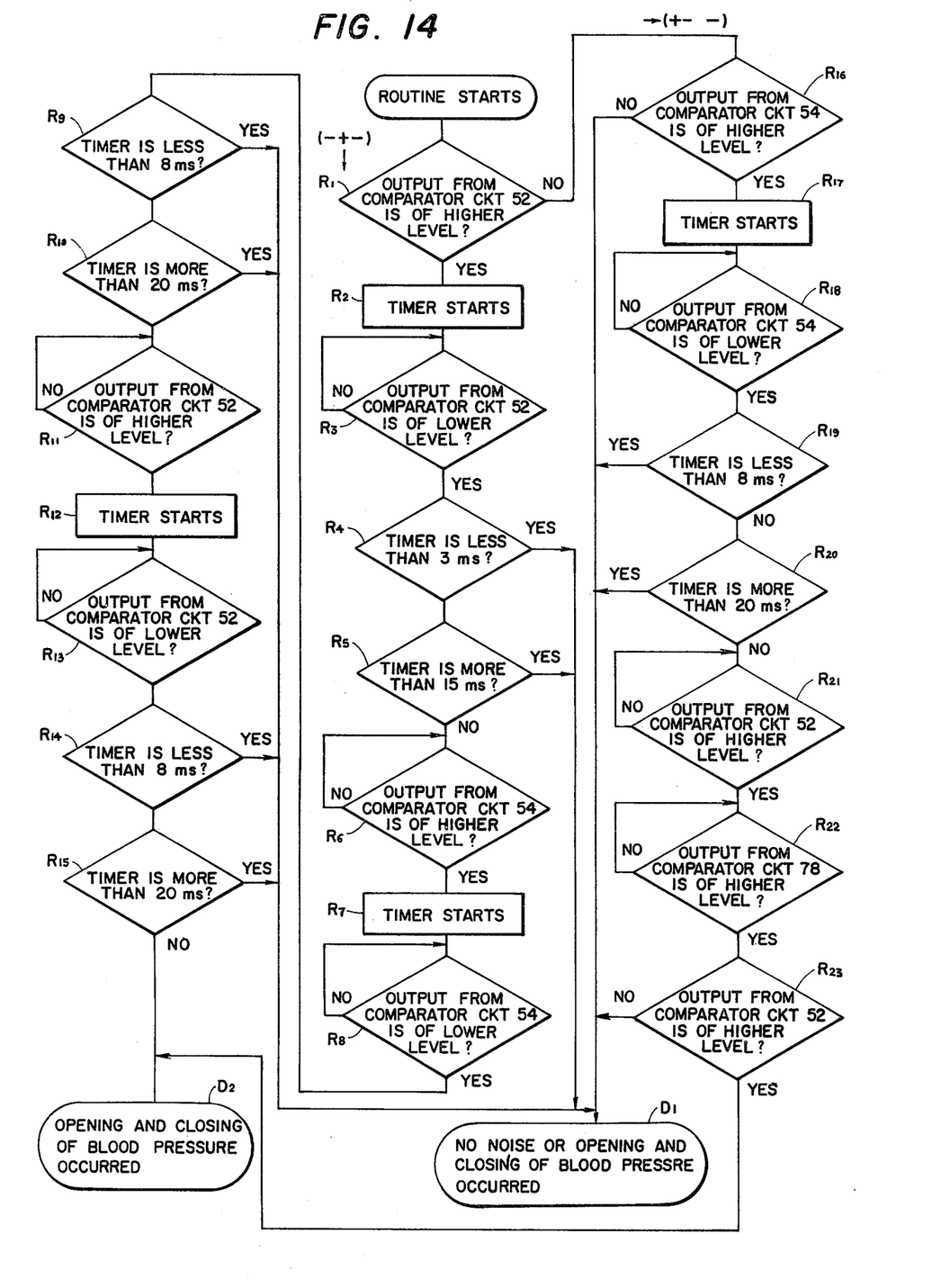
FIG. 14 is a flowchart showing the procedure for the operation of detecting the K pulse.

The detection of the K pulse under a program follows the procedure, for example, shown in FIG. 14. That is, in a step $R_1$, it is checked whether or not the output from the comparator circuit 52 has become high in level. Where it has become high, the routine for selecting the K pulse with the negative, positive and negative pulses is started and, at a step $R_2$, a timer is started. This timer is obtained by additing clock pulses of the CPU 81 in a predetermined address of the memory 82. In a step $R_3$, it is checked whether or not the output from the comparator circuit 52 has become low in level. Where it has become low in level, the timer started previously is checked as to whether or not the time elapsed is less than 3 milliseconds in a step $R_4$. In the case of less than 3 milliseconds, it is decided the output from the comparator circuit 52 is noise to provide the decision result $D_1$, or it is decided that opening and closing of the blood vessel have not occurred yet. If it is decided that the time elapsed is more than 3 milliseconds and that the output from the comparator circuit 52 is the negative pulse (FIG. 3), the timer is checked as to whether or not more than 15 milliseconds have passed in the next step $R_5$. In the case of more than 15 milliseconds, the output from the comparator circuit 52 is regarded as a noise or it is regarded that opening and closing of the blood vessel have not occurred yet. In the case of less than 15 milliseconds, it is detected in a step $R_6$ whether the level of the output from the positive pulse detecting comparator circuit 54 is high or not. Where this output is of the high level, the timer is re-started in a step $R_7$. And in the next step $R_8$, it is checked whether the level of the output from the comparator circuit 54 has become low or not. Where the level is low, the timer is checked as to whether or not the elaspsed time is less than 8 milliseconds in a step $R_9$. In the case of more than 8 milliseconds, the output from the comparator circuit 54 is decided the positive pulse 58 (FIG. 3) and the operation proceeds to the next step $R_{10}$, in which the timer is checked as to whether the time elapsed is more than 20 milliseconds or not. In a step $R_{11}$, if the output from the comparator circuit 52 is decided to be of the high level within 20 milliseconds, the time is started again in the next step $R_{12}$ and, in a step $R_{13}$, it is checked whether the output from the comparator circuit 52 becomes of the low level. Where it becomes of the low level, the timer is checked as to whether or not the time elapsed is less than 8 milliseconds in a step $R_{15}$. In the case of more than 8 milliseconds, the output from the comparator circuit 52 is decided a positive pulse. Further, in the step $R_{15}$, the timer is checked as to whether or not the time elapsed is more than 20 milliseconds. Where it is less than 20 milliseconds, the output from the comparator circuit 52 is decided the positive pulse 58 (FIG. 3), that is, a decision result $D_2$ is obtained which indicates that the K pulse has been obtained.

In this manner, the K pulse is detected by watching the negative, positive and negative pulses shown in FIG. 3. When the output from the comparator circuit 52 is decided to be of the low level in the step $R_1$, the operation is shifted to the K pulse detection routine described previously with regard to FIG. 7. That is, in a step $R_{16}$, it is checked whether the output from the comparator circuit 54 is of the high level or not. If it is of the high level, the timer is started in a step $R_{17}$ and, in the next step $R_{18}$, it is checked whether the output from the comparator circuit 54 becomes of the low level or not. Where it becomes of the low level, the timer is checked as to whether the time elapsed is less than 8 milliseconds or not in a step $R_{19}$. In the case of more than 8 milliseconds, the output from the comparator circuit 54 is decided to be the positive pulse 57 (FIG. 7). In the next step $R_{20}$, the time is checked as to whether or not more than 20 milliseconds has passed and, in a step $R_{21}$, it is checked whether the output from the comparator circuit 52 becomes of the high level within 20 milliseconds or not. In the case of the high level, it is checked whether or not the output from the comparator circuit 78 is of the high level in a step $R_{22}$. Where the abovesaid output is of the high level, the high level of the output from the comparator circuit 78 is checked again in a step $R_{23}$ for verification. And when this output is verified to be of the high level, it is decided that the K pulse has been obtained, and the decision result $D_2$ is obtained.

When the K pulse has been detected as described above, instructions for closing the valve 86 in FIG. 9 are issued in the step $S_{10}$ in FIG. 10 to hold the cuff pressure constant, and in the next step $S_{11}$, it is decided whether or not the K pulse is obtained within 1 second. Where the K pulse is not obtained within 1 second, the detected K pulse is decided to be a noise and the operation returns to the step $S_6$ to open the valve 86 to start the K pulse detecting operation again. Where the K pulse is detected again within 1 second in the step $S_{11}$, it is decided to be a correct K pulse obtained for the first time. Since the cuff pressure at this time is the highest blood pressure, the pressure detected by the pressure detector 16 is read in the CPU 81, and stored in the latch circuit 113 through the output bus 84, and then displayed as the highest blood pressure by a display 114.

Next, in a step $S_{13}$, the valve 87 is opened for a certain period of time, for instance, 100 milliseconds, thereby lowering the pressure of the blood-pressure cuff, for example, by 2 mmHg. In the next step $S_{14}$, the timer is started for 2 seconds, and then the K pulse is detected in the next step $S_{15}$. Upon detection of the K pulse, the operation returns to the step $S_{13}$ to open the valve 87 for a certain period of time, lowering the cuff pressure by a certain value. Thus, each time the K pulse is obtained, the pressure of the cuff is decreased. Accordingly, as indicated by the curve 94 in FIG. 11, the cuff pressure begins to be decreased at the moment $t_2$, and when the K pulse is detected for the first time at the moment $t_3$ in the step $S_{11}$, the pressure is held at the value Pmax at this time. And under such conditions, the K pulse is obtained again and verified to obtain the highest blood pressure Pmax. From this moment $t_4$, the cuff pressure is decreased by a certain value each time the K pulse is obtained.

Where the K pulse is not obtained within two seconds after the cuff pressure is lowered, the timer turns off, and this is detected in a step $S_{16}$. This indicates that the flow of the blood has become normal and hence no K pulse is produced, and the cuff pressure is the lowest in a step $S_{17}$, the pressure detected by the pressure detector 16 is stored in the latch circuit 115 through the CPU 81, and displayed as the lowest blood pressure on the display 116. Thereafter, in a step $S_{18}$, the valves 86 and 87 are opened, completing the blood pressure measuring operation.

Figure 11:
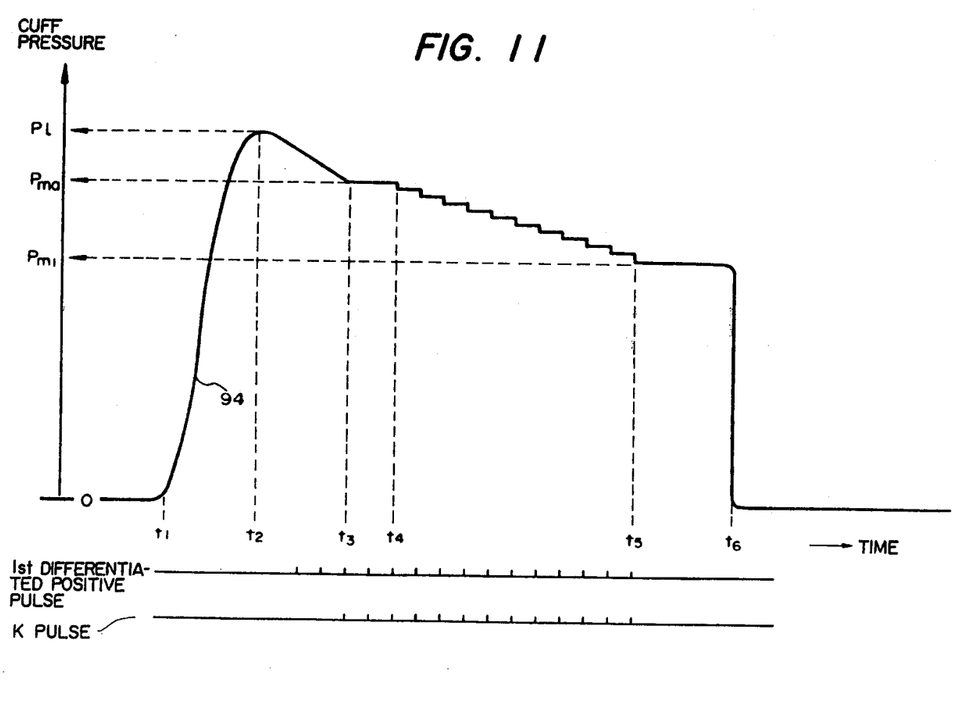
FIG. 11 is a diagram showing the pressure fluctuation with the lapse of time.

As illustrated in FIG. 11, when no K pulse is detected within 2 seconds after the cuff pressure is decreased to a value Pmi at the moment $t_5$, the pressure is decided to be the lowest blood pressure and, at this moment $t_5$, the valves 86 and 87 are opened to decrease the cuff pressure to zero. While the cuff pressure varies, the output from the pressure sensor 21 is recorded by the analog recorder 20. At the same time, each time the K pulse is detected, the cuff pressure is recorded on one marginal portion of the analog recording paper 101. In the illustrated example, recording of the cuff pressure is started a little before the detection of the first K pulse. That is, since the pressure sensor 21 responds to the pressure of a blood pulse that the blood tends to flow a little before the K pulse is obtained, that is, the blood actually starts to flow a positive pulse is obtained in the output resulting from one differentiation of the output from the pressure sensor 21. This positive pulse is also obtained at each detection of the K pulse, as seen from the waveforms depicted in FIGS. 3B and 7B. Accordingly, in FIG. 9, it is detected by a comparator circuit 117 whether the output from the differentiation circuit 38 has a predetermined level or not, and this output is decided to be of high or low level depending upon whether its level is higher or lower than the predetermined level. In the recording routine FIG. 10, in the step $S_{19}$ following the time recording step $S_8$, it is checked whether or not the positive pulse is derived from the output of the comparator circuit 117. When the positive pulse is obtained from the first differentiation, the output from the pressure detected 16 at this time is taken in the CPU 81 in a step $S_{20}$, and character codes indicating the numerical value of the abovesaid output are sequentially supplied to a printing latch circuit 95 to record the cuff pressure as indicated by a record 118 in FIG. 12, as is case with the recording of time. The recording at each detection of the positive pulse in the first differentiated output is repeated until the detection of completion accompanying the operation of the step $S_{18}$. As shown in FIG. 11, the positive pulse of the first differentiation is obtained from a moment a little before the moment $t_3$ at which the detection of the K pulse begins. Upon detection of completion of the operation at a step $S_{21}$, a recording paper drive motor 96 in the recorder 20 is stopped in a step $S_{22}$.

As described above, by simply operating the start switch 85, the blood pressure is automatically measured and the measured value is automatically displayed on the displays 114 and 116 and, at the same time, recorded on the recording paper 101. In place of manually controlling the start switch 85, it is also possible to control an automatic start switch 119, for example, in the case of checking respiration or pulsation of a post-operative patient. That is, when a change is detected in the patient condition, blood pressure measuring instructions are issued by the detected output to control the automatic start switch 119. The switch 119 is periodically supervised by the CPU 81 through a gate 80. Upon detection of turning on of the switch 119, the blood pressure measurement is automatically achieved by the same operations as those in the case of the switch 85 being turned on.

Also, it is possible to periodically achieve the blood measurement of the post-operative patient. To this end, a digital switch 121 for setting the measurement time is provided, and is adapted to set a desired value of, for example, 00 to 60 minutes in the unit of minute. The set value is periodically applied to the CPU 81 through the gate 122 and, at the same time, the clock signal of the timer 99 is applied through gate 98 to the CPU 81. The set value is added to the clock signal and the added value is stored in the memory 82. The stored value is compared with the clock signal of the timer 99 and, at each coincidence, the blood pressure measuring operation is performed and, the addition of the set value to the clock signal and storing of the added value are repeated. For instance, when the set value of the digital switch 121 is 15 minutes, the blood measurement takes place every 15 minutes.

As has been described in the foregoing, with the blood pressure measuring instrument of this invention, since the pressure of the flow of the blood is measured by the pressure sensor, a high accuracy of the measurement can be obtained. Though depending upon the resolving power of the pressure detector 16, measurement with an accuracy of about ±6 mmHg is relatively easy. Further, unlike in the case of hearing a sound, external noises are hardly picked up and can be easily discerned. Moreover, the parts forming the instrument are relatively simple and inexpensive and commercially available. The position of the pressure sensor 21 is such that pulsebeats can be obtained, and can be determined by anyone relatively easily. Even if the pressure sensor 21 is disposed a little out of the correct position, the pressure of the blood in the blood vessel is still transmitted to the pressure sensor 21, so the blood pressure can be measured accurately. And even if the pressure sensor 21 shifts a little out of position during the measurement, the recorded waveform remains unchanged and the amplitude changes only slightly as a whole. Accordingly, the measurement is accurate, very easy and almost free from errors. Moreover, if no pulse waveform is found in the analog record, it can be known that the sensor 21 is disposed too much apart from the position where the pulsebeats are obtained. Accordingly, anyone can decide whether the pressure sensor 21 is in position or not, and can perform accurate measurement. Further, even when the blood pressure becomes very low, the waveform of the flow of the blood appears, so that the blood pressure of a patient during or after an operation can be measured. In this regard, the present invention is advantageous as compared with the case of hearing the pulsebeats through a stethoscope.

Moreover, the measurement can be automatically achieved not only by manually effecting the respective operations but also by turning on the start switch and the measured values are displayed on the display and in addition recorded on the recording paper, so that the recorded waveforms can be reviewed after the measurement. Since the time of measurement is also recorded, it can be known how the blood pressure changes all day long. The detection of the K pulse by processing the output waveform of the pressure sensor involves detection of the pulse 45 having the gap 32 described previously in connection with FIG. 3. This means that the pattern of the pulse 45 is clearly recognizable, so that by obtaining the correlation between the reference pattern of the abovesaid pulse waveform and the output waveform of the pressure sensor 21, the cuff pressure at the moment of obtaining an especially high correlation can be decided to be the highest blood pressure. And the cuff pressure obtained when such a high correlation is no longer detected is the lowest blood pressure.

As described above, in the case of achieving the program controlled measurement, when starting instructions are issued, the output from the amplifier 91 in FIG. 9 is measured and stored and the cuff pressure is measured using the stored value as "zero", i.e. as the reference value. With such an arrangement, the pressure sensor 21 and a drift due to a temperature change of the pressure sensor 21 and a drift of the amplifier 91 exist, but accurate measurement results can be obtained without being affected by them. This means that even if the sensor for converting the detected pressure of the pressure detector 16 into an electric signal is an inexpensive one, accurate measurement can nevertheless be performed.

It will be apparent that many modifications and variations may be effected without departing from the scope of the novel concepts of this invention.

What is claimed is:

1. A blood pressure measuring instrument comprising:
   pressure means for applying a pressure by a cuff to a blood vessel of a test subject from the outside thereof;
   pressure changing means for gradually changing the pressure;
   a pressure sensor disposed in contact with the test subject beneath the cuff for converting into an electric signal a pressure change resulting from movement of the blood vessel while the pressure to the blood vessel is gradually changed;

a differentiation circuit coupled to said pressure sensor for differentiating twice the converted output from the pressure sensor;

identifying means coupled to said differentiation circuit for detecting the generation of a characteristic waveform consisting of three closely successive pulses comprising a first-polarity pulse followed by a second-polarity pulse which is in turn followed by another first-polarity pulse; and means responsive to the output of said identifying means for measuring, as the highest and lowest blood pressures respectively, the pressures applied to the cuff by the pressure means at the first and last detections of said characteristic waveform by the identifying means.

2. A blood pressure measuring instrument according to claim 1, which further includes an auxiliary circuit for detecting in one pulse of the converted output from the pressure sensor that a first-polarity pulse is produced close to a second-polarity pulse in the output waveform of the differentiation circuit and that the output waveform obtained by differentiating the converted output once at the same time that said first-polarity pulse occurs is a pulse of said first-polarity, and wherein the logical sum of the output from the auxiliary circuit and the output of said identifying means indicating the successive generation of the three pulses within a predetermined period of time is used to control operation of said measuring means.

3. A blood pressure measuring instrument according to claim 1, which includes an analog recorder for recording the output from the pressure sensor.

4. A blood pressure measuring instrument according to claim 3, which includes a digital recorder for recording the value of pressure applied by the pressure means on an analog recording paper.

5. A blood pressure measuring instrument according to claim 1, wherein the identifying means comprises combination of a comparator circuit with a logic circuit.

6. A blood pressure measuring instrument according to claim 1, where the identifying means is composed of a comparator circuit for shaping the output from the differentiation circuit, and a programmed arithmetic operation processor for periodically monitoring the output from the comparator circuit to determine whether said output constitutes a series of the first-polarity pulse closely followed by the second-polarity pulse which is in turn closely followed by another first-polarity pulse.

7. A blood pressure measuring instrument according to claim 1, which includes a control circuit supplied with starting instructions to sequentially perform the operations of controlling the pressure means by adding thereto a pressure up to a predetermined value, gradually reducing the pressure upon detection of the predetermined value, and measuring the pressure of the pressure means.

8. A blood pressure measuring instrument according to claim 7, wherein the control circuit is composed of a memory having a control program stored therein, and an arithmetic operation processor operating in accordance with said program.

9. A blood pressure measuring instrument according to claim 7, which includes means for lowering the pressure of the pressure means by a predetermined value each time said characteristic waveform is detected by the identifying means.

* * * * *